United States Patent
Reuter (12)

(10) Patent No.: US 8,470,072 B2
(45) Date of Patent: Jun. 25, 2013

(54) METHOD AND APPARATUS FOR THE CONTROL OF GAS PRESSURE IN GAS CHROMATOGRAPHY COLUMNS

(75) Inventor: Norbert Alfred Reuter, Middleburg (NL)

(73) Assignee: Bruker Daltonik, GmbH, Bremen (DE)

( * ) Notice: Subject to any disclaimer, the term of this patent is extended or adjusted under 35 U.S.C. 154(b) by 380 days.

(21) Appl. No.: 12/783,996

(22) Filed: May 20, 2010

(65) Prior Publication Data
US 2011/0016951 A1    Jan. 27, 2011

(30) Foreign Application Priority Data
May 29, 2009  (EP) ...................................... 09251437

(51) Int. Cl.
*B01D 53/02*  (2006.01)

(52) U.S. Cl.
USPC .................. 95/89; 96/103; 96/105; 73/23.42

(58) Field of Classification Search
CPC ....................................................... G01N 30/32
USPC ........ 96/101, 103, 105; 95/82, 89; 73/23.35, 73/23.41, 23.42
See application file for complete search history.

(56) References Cited

U.S. PATENT DOCUMENTS

| | | | |
|---|---|---|---|
| 4,976,750 A * | 12/1990 | Munari | ............................ 95/19 |
| 5,163,979 A | 11/1992 | Patrick et al. | |
| 5,476,000 A | 12/1995 | Henderson | |
| 5,859,360 A | 1/1999 | Magni | |
| 2003/0106363 A1 | 6/2003 | Sacks et al. | |
| 2004/0149012 A1 | 8/2004 | Furukawa | |
| 2007/0125233 A1 | 6/2007 | Bostrom | |

* cited by examiner

*Primary Examiner* — Robert Clemente
(74) *Attorney, Agent, or Firm* — ROBIC, LLP

(57) ABSTRACT

The pressure of a carrier gas entering a gas chromatography (GC) column is controlled by increasing or decreasing the gas pressure over a pressure change cycle by which a desired gas pressure is obtained while avoiding pressure pulses in the column. The pressure change cycle may follow a function that dictates the rate of pressure change. A gas flow controller that controls the gas pressure at the inlet or head of the column may be operated to implement the pressure change cycle. The gas flow controller may be controlled by an electronic controller.

12 Claims, 2 Drawing Sheets

METHOD AND APPARATUS FOR THE CONTROL OF GAS PRESSURE IN GAS CHROMATOGRAPHY COLUMNS

BACKGROUND

The present invention relates generally to gas chromatography and particularly to controlling gas pressure in conjunction with gas chromatography. Gas chromatography (GC) entails the analytical separation of a vaporized or gas-phase sample. In a GC system, the sample is injected into a chromatographic column and is carried through the column by a chemically inert carrier gas such as hydrogen, helium or nitrogen. The carrier gas is utilized as the mobile phase for elution of the analyte sample in the column.

The carrier gas is typically introduced into the column at a location near where the sample is injected, e.g., at the head of the column, and thus carries the sample through the column. The column is typically housed in a thermally controlled oven. The column may be constructed of stainless steel, glass, fused silica, Teflon®, or the like. The column may be of the packed or open tubular (capillary) type. The column contains a stationary phase (particles, films or layers of a selected composition) by which different components of the sample are retained differently. Thus, as the sample flows through the column it becomes separated into discrete components of differing analytical (qualitative and/or quantitative) significance.

The eluent from the column flows to a detector provided with the GC system. Various types of detectors may be employed such as, for example, a flame ionization detector (FID), thermal conductivity detector (TCD), etc. The choice of detector often depends on the sample being analyzed. Moreover, the type of carrier gas utilized often depends on the type of detector utilized. Generally, the detector is of a type responsive to a property of the separated analytes (e.g., concentration) and converts the outputted flow of separated analytes to electrical measurement signals, which are then transmitted to a data processor. The data processor derives peak information or other useful analytical information from the measurement signals received.

A GC system typically utilizes a gas flow (flow rate and/or pressure) regulator to control (switch on and off) the flow of carrier gas to the GC column. For the GC system to operate properly, the carrier gas must flow through the column at a particular working pressure (i.e., column head pressure). Conventionally, the gas flow regulator attempts to increase (switch on) or decrease (switch off) the pressure to the working (set-point) pressure as fast as possible. Moreover, the carrier gas may be provided by a carrier gas supply source that is initially pressurized at a pressure much different from the set-point pressure, and/or the GC column may initially be at ambient pressure which may be substantially different from the set-point pressure.

Thus, due to the rapid changing of the gas pressure, the compressibility and expansion of the carrier gas, and the fact that the working pressure may differ substantially from the ambient pressure, the conventional operation of the gas flow regulator may cause pressure pulses in the column. Such pressure pulses may cause particles of the stationary phase contained in the column to become loose and flow through the column. The loose particles may accumulate and block flow through the column, become lost, and generally render the column unusable.

This is particularly true in the case of Porous Layer Open Tubular (PLOT) capillary columns. A PLOT column is typically constructed of fused silica or steel tubing. The inner wall of the tubing is coated with different porous adsorbents held on the inner wall mainly by London/Van der Waals forces. Particles from the porous layer may become loosened by pressure pulses.

In view of the foregoing, there is a need for controlling the pressure of a carrier gas flowing into a GC column in a manner that avoids or at least substantially reduces pressure pulses.

SUMMARY

In accordance with the principles of the invention, at an initial time t=0, a flow of carrier gas entering a gas chromatography (GC) column through a carrier gas conduit is switched on. At the initial time, the pressure of the carrier gas at the entrance of the GC column is an initial gas pressure. The gas pressure is gradually increased from the initial gas pressure to a set-point gas pressure over a pressure increase cycle of duration $t=t_{cycle}$. During the pressure increase cycle, the carrier gas flows into the GC column without pressure pulses, and after the pressure increase cycle, the carrier gas flows into the GC column at the set-point gas pressure.

According to one embodiment, after increasing the gas pressure to the set-point gas pressure over the pressure increase cycle, the flow of carrier gas is switched off, by gradually decreasing the gas pressure over a pressure decrease cycle from the set-point gas pressure to a pressure at which the carrier gas ceases to flow. During the pressure decrease cycle, the carrier gas flows into the GC column without pressure pulses.

According to another embodiment, a gas chromatography (GC) apparatus includes a GC column with a GC column entrance, a carrier gas conduit communicating with the GC column entrance, a gas flow controller communicating with the carrier gas conduit and configured for switching on a flow of carrier gas to the GC column entrance, and an electronic controller in signal communication with the gas flow controller. The electronic controller includes circuitry for controlling the pressure controller to switch on the flow of carrier gas according to a pressure increase cycle wherein the gas flow controller gradually increases the gas pressure from an initial gas pressure to a set-point gas pressure over a pressure increase cycle of duration $t=t_{cycle}$, wherein, during the pressure increase cycle, the carrier gas flows into the GC column without pressure pulses, and after the pressure increase cycle the carrier gas flows into the GC column at the set-point gas pressure.

According to still another embodiment, the gas flow controller is configured for switching off the flow of carrier gas by gradually decreasing the gas pressure over a pressure decrease cycle from the set-point gas pressure to a pressure at which the carrier gas ceases to flow, wherein during the pressure decrease cycle the carrier gas flows into the GC column without pressure pulses.

BRIEF DESCRIPTION OF THE DRAWINGS

For a better understanding of the present invention an embodiment will now be described by way of example, with reference to the accompanying drawings, in which.

$$P(t) = P_{end} * \exp\{(\tfrac{1}{3})(t_{actual} - t_{cycle})\} \text{ and where } dp/p = 0.2.$$

DETAILED DESCRIPTION

Figure 1:
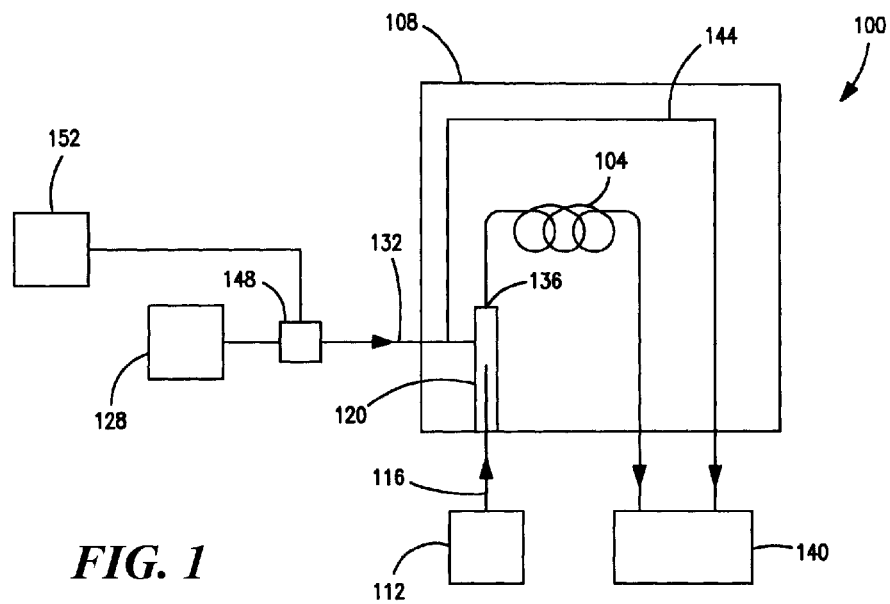
FIG. 1 is a schematic view of an example of a gas chromatographic system that may be employed in conjunction with the invention.

FIG. 1 schematically illustrates a few basic components of a gas chromatograph (GC) apparatus, or system 100, as an example of the type of apparatus (or system) that may be utilized in conjunction with the invention. The GC apparatus 100 includes a chromatographic column 104 enclosed in an enclosure 108 that often functions as an oven for heating the column 104. A portion of the column 104 may be coiled to accommodate a desired length while minimizing the size of the enclosure 108. A sample supply source or injection system 112 includes a syringe (not shown) or other fluid moving means to introduce an analyte sample into the column 104 via a sample line 116 communicating with an interface 120 such as a fitting mounted through the wall of the enclosure 108.

Sample injection may be carried out on an automated, semi-automated, or manual basis. A carrier gas supply system 128 establishes a flow of a carrier gas, such as hydrogen, helium or nitrogen, into the interface 120 through a carrier gas supply line 132 (e.g., a suitable conduit such as a tube or pipe) at a regulated flow rate/pressure. The flow of carrier gas is regulated by a gas flow regulator or controller 148. In the schematic illustration, the gas flow regulator 148 may represent one or more components (e.g., pressure regulator, flow controller, etc.). Generally, the gas flow regulator 148 may have any suitable design that is capable of switching the flow of carrier gas between on and off states and regulating flow rate by regulating pressure. The gas flow regulator 148 may also be capable of sensing the carrier gas pressure and providing a readout signal thereof.

The sample is transported by the carrier gas into an entrance 136 of the GC column 104 and through the column 104, and the eluted components exit the column 104 to a detector 140 to generate analytical signals for processing by a data acquisition system (not shown). Depending on the type of detector 140 utilized, the flow of carrier gas may be split into a reference gas line 144 that also runs through the heated enclosure 108 to the detector 140.

The GC apparatus 100 also includes a suitable electronic controller 152 that may be utilized to control one or more of the operative components briefly described above. The electronic controller 152 may be electronic processor-based and may be capable of executing instructions contained in software. Generally, the electronic controller 152 schematically illustrated in FIG. 1 may include hardware, firmware, software, or a combination of two of more of the foregoing. The electronic controller 152 is configured for transmitting control signals to the gas flow regulator 148 to control the switching on and off of the carrier gas and the gas pressure. The electronic controller 152 may also be configured for receiving measurement signals from the gas flow regulator 148 (or from a separately provided sensor) that are indicative of the carrier gas pressure at the column head, whereby the electronic controller 152 makes decisions on how to control the carrier gas flow based in part of such measurement signals. The electronic controller 152 may also communicate (not shown) with other components such as the sample injection system 112 and carrier gas supply system 128 as needed for coordinating their respective operations with that of the gas flow regulator 148.

In accordance with the present teachings, the gas flow regulator 148 controls carrier gas pressure in a manner that eliminates or at least substantially reduces the occurrence of gas pulses in the column 104, thereby eliminating or at least substantially preventing particles of the stationary phase of the column 104 from loosening and causing problems such as noted earlier in this disclosure.

To flow the sample through the column 104, the flow of carrier gas must be switched on and the pressure of the carrier gas must be increased to a working (set-point) pressure desired for the particular experiment being carried out. Just before switching on the carrier gas flow, the initial gas pressure at the entrance of the column 104 may be substantially different from the desired set-point gas pressure. For instance, the initial gas pressure may be equal or approximately equal to the pressure of the ambient surroundings. Upon switching on the carrier gas flow, the gas flow regulator 148 gradually increases the carrier gas pressure from the initial gas pressure to the set-point gas pressure over a period of time referred to as a gas pressure increase cycle.

During the gas pressure increase cycle, the rate of increase in gas pressure may be dictated by a gas pressure change function. For instance, the electronic controller 152 may control the gas flow regulator 148 in accordance with this gas pressure change function via control signals. A user may input a desired set-point gas pressure to the electronic controller 152 which then implements the gas pressure change function based on the set-point pressure.

The electronic controller 152 may determine other parameters of the gas pressure change function such as, for example, the total duration of the gas pressure increase cycle time, based on such factors as the set-point pressure, the actual gas pressure at a given point in time, the gas temperature, the type of carrier gas, etc. In some implementations, the electronic controller 152 may select a gas pressure change function from a plurality of available functions as being the function optimal for a given set of conditions. Alternatively, the user may select the gas pressure change function.

Generally, the gas pressure change function (rate of pressure increase), and the duration of the cycle over which the carrier gas flow is controlled by the gas pressure change function, are designed such that the increase in gas pressure from the initial condition to the set-point gas pressure is gradual enough to avoid pressure pulses. The total cycle time during which the gas pressure change function is implemented may vary, depending on factors such as the initial difference between the actual gas pressure and the target set-point pressure. In typical implementations, the cycle time ranges from 0 to 300 seconds. The rate of pressure increase may be linear with time or may be non-linear with time. In the case of a linear function, the slope of the function may be selected as appropriate to ensure that the pressure change is gradual enough to avoid pressure pulses during the pressure increase cycle. As an example of a non-linear function, the rate of pressure increase may be exponential such that during the beginning portion of the gas pressure increase cycle the gas pressure changes relatively slowly, and subsequently the gas pressure changes faster as the difference between the set-point pressure and the actual pressure (at a given instance of time during the pressure increase cycle) becomes smaller. One specific, yet non-limiting, example of an exponential function is the following:

$$P(t) = P_{end} * \exp\{x*(t_{actual} - t_{cycle})\}$$

where P(t) is the actual gas pressure at a given time during the pressure increase cycle, $P_{end}$ is the set-point gas pressure, $t_{actual}$ is a given point in time during the pressure increase cycle, and $t_{cycle}$ is the cycle time (the total duration of the pressure increase cycle), and x is a steepness factor selected to influence the steepness of the exponential rate of pressure change. For example, x may be equal to 1/y where y is an integer or any other number. In one specific, yet non-limiting, example of a suitable steepness factor, x=⅓(y=3), resulting in the following exponential function:

$$P(t)=P_{end}*\{(\frac{1}{3})*(t_{actual}-t_{cycle})\}$$

Moreover, the rate of pressure change during the pressure increase cycle may be implemented such that in a given interval of time, the pressure change $P_{actual}-P_{previous}$ relative to $P_{actual}$, or more generally dp/p, is a constant k that is equal to or less than a desired number so as to define the steepness of the function. Thus:

$$(P_{actual}-P_{previous})/P_{actual}=k$$

where $P_{actual}$ is the gas pressure at a given point in time during the pressure increase cycle, $P_{previous}$ is the gas pressure at a previous point in time, and k is a constant selected to ensure that the pressure change interval is gradual enough to avoid pressure pulses. The constant k may range from 0 to 1.

It will be appreciated by persons skilled in the art that other non-linear functions besides exponential functions may be implemented. An additional example is a parabolic function, which may be implemented such that dp/t=constant although dp/p would not be constant.

It will also be appreciated that gas pressure change functions, such as just described, may also be utilized to determine the rate of pressure decrease over the duration of a pressure decreasing cycle. A pressure decreasing cycle may be implemented by the gas flow regulator 148 (which again may be controlled by the electronic controller 152) when it is desired to switch off the flow of carrier gas to the GC column 104. By implementing a gas pressure change function instead of simply shutting down the carrier gas supply, the gas pressure may be gradually decreased to avoid pressure pulses that might otherwise result from a rapid decrease in gas pressure. A linear or non-linear function as described above may be utilized to control the rate of decrease in the gas pressure. Similarly, the pressure decreasing function utilized may one in which $(P_{previous}-P_{actual})/P_{actual}$ is equal to or does not exceed a selected constant value.

Figure 2:
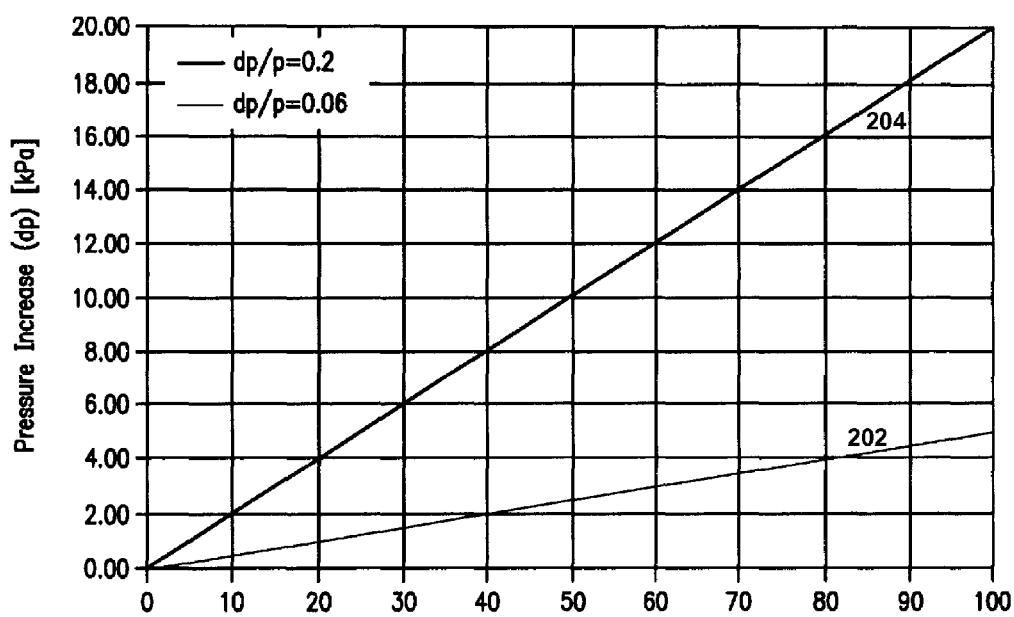
FIG. 2 is a plot of pressure increase dp as a function of pressure p for two examples, dp/p=0.2 and dp/p=0.05.
Figure 3:
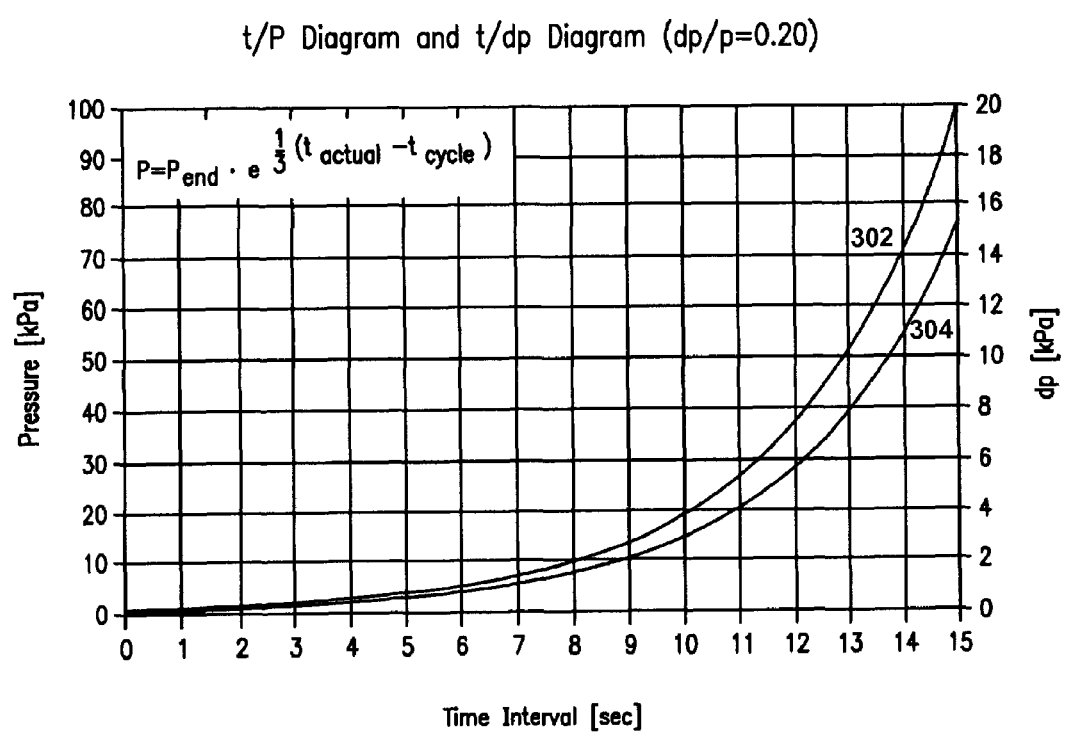
FIG. 3 is a plot of pressure as a function of time p/t and pressure increase as a function of 25 time dp/t in the case where pressure is increased according to the exponential function.

FIGS. 2 and 3 provide non-limiting examples of pressure changing functions that may be utilized for implementing a gas pressure change cycle when switching on (increasing pressure) or switching off (decreasing pressure) the flow of carrier gas. FIGS. 2 and 3 are specific to the case of increasing pressure, but persons skilled in the art will appreciate how to adapt such functions to the case of decreasing pressure. FIG. 2 is a plot of pressure increase dp as a function of pressure p for two examples, dp/p=0.2 (line 202) and dp/p=0.05 (line 204). FIG. 3 is a plot of pressure as a function of time p/t (line 302) and pressure increase as a function of time dp/t (line 304) in the case where pressure is increased according to the exponential function $P(t)=P_{end}*\exp\{(\frac{1}{3})*(t_{actual}-t_{cycle})\}$ and where dp/p=0.2.

From the foregoing, it can be seen that the pressure change cycles (pressure increase and pressure decrease) disclosed herein are useful for eliminating pressure pulses in a GC column. Hence, damage to the GC column is prevented and its usable lifetime prolonged. Moreover, contamination of the GC system by loose particles is avoided. As a result, less maintenance to the GC system is necessary and the system's up-time increases.

In general, the term "communicate" (for example, a first component "communicates with" or "is in communication with" a second component) is used herein to indicate a structural, functional, mechanical, electrical, optical, magnetic, ionic or fluidic relationship between two or more components or elements. As such, the fact that one component is said to communicate with a second component is not intended to exclude the possibility that additional components may be present between, and/or operatively associated or engaged with, the first and second components. It will be understood that various aspects or details of the invention may be changed without departing from the scope of the invention. Furthermore, the foregoing description is for the purpose of illustration only, and not for the purpose of limitation.

What is claimed is:

1. A method for controlling a pressure of a carrier gas entering a gas chromatography (GC) column, comprising:
   (a) initiating a flow of carrier gas having initial gas pressure into an entrance of a GC column of the porous layer open tubular type, wherein the initial gas pressure is one of an ambient pressure and an initial pressure of a carrier gas supply; and
   (b) gradually increasing the gas pressure from the initial gas pressure to a set-point gas pressure, which represents a working pressure, over a pressure increase cycle of duration $t=t_{cycle}$, so that during the pressure increase cycle the carrier gas flows into the GC column without pressure pulses, and after the pressure increase cycle the carrier gas flows into the GC column at the set-point gas pressure.

2. The method of claim 1, wherein the gas pressure increases at a rate that is one of linear with time and non-linear with time.

3. The method of claim 1, wherein the gas pressure is increased according to a function: $P(t)=P_{end}*\exp\{x*(t_{actual}-t_{cycle})\}$, where $P_{end}$ is the set-point gas pressure, $t_{cycle}$ is the duration of the pressure increase cycle, $t_{actual}$ is an actual time during the pressure increase cycle, and x is a steepness factor.

4. The method of claim 3, where x=1/y and y≧1 is an integer.

5. The method of claim 1, wherein the gas pressure is increased according to the formula $(P_{actual}-P_{previous})/P_{actual}=k$, where $P_{actual}$ is an actual gas pressure at a given point in time during the pressure increase cycle and $P_{previous}$ is the gas pressure at a previous point in time during the pressure increase cycle, and k is a constant.

6. The method of claim 5, wherein the constant k ranges from 0 to 1.

7. The method of any one of claims 1-6, wherein the duration $t_{cycle}$ of the pressure increase cycle ranges from 0 to 300 seconds.

8. The method of claim 1, further comprising, after increasing the gas pressure to the set-point gas pressure over the pressure increase cycle, switching off the flow of carrier gas by gradually decreasing the gas pressure over a pressure decrease cycle from the set-point gas pressure to a pressure at which the carrier gas ceases to flow, so that during the pressure decrease cycle the carrier gas flows into the GC column without pressure pulses.

9. The method of claim 8, wherein the pressure decrease rate is one of linear with time and non-linear with time.

10. The method of claim 8, wherein gas pressure is decreased according to the formula $(P_{previous}-P_{actual})/P_{actual}=k$, where $P_{actual}$ is an actual gas pressure at a given point in time during the pressure decrease cycle, $P_{previous}$ is the gas pressure at a previous point in time during the pressure decrease cycle, and k is a constant.

11. A method for controlling a pressure of a carrier gas entering a gas chromatography (GC) column, comprising:

(a) initiating a flow of carrier gas having an initial gas pressure into an entrance of the GC column;

(b) gradually increasing the gas pressure from the initial gas pressure to a set-point gas pressure over a pressure increase cycle of duration $t=t_{cycle}$ so that during the pressure increase cycle the carrier gas flows into the GC column without pressure pulses, and after the pressure increase cycle the carrier gas flows into the GC column at the set-point gas pressure; and (c) introducing a sample into the flow of carrier gas and, while maintaining the flow of carrier gas at the set-point gas pressure, flowing the sample and the carrier gas into the GC column to perform an analytical separation of the sample.

12. A method for controlling a pressure of a carrier gas entering a gas chromatography (GC) column, comprising:

(a) initiating a flow of carrier gas having initial gas pressure into an entrance of the GC column; and (b) gradually increasing the gas pressure at a rate that is non-linear with time from the initial gas pressure to a set-point gas pressure over a pressure increase cycle of duration $t=t_{cycle}$, so that during the pressure increase cycle the carrier gas flows into the GC column without pressure pulses, and after the pressure increase cycle the carrier gas flows into the GC column at the set-point gas pressure.

\* \* \* \* \*

UNITED STATES PATENT AND TRADEMARK OFFICE
CERTIFICATE OF CORRECTION

PATENT NO.        : 8,470,072 B2
APPLICATION NO.   : 12/783996
DATED             : June 25, 2013
INVENTOR(S)       : Norbert Alfred Reuter It is certified that error appears in the above-identified patent and that said Letters Patent is hereby corrected as shown below:

Title page, Item [73], Assignee, replace "Bruker Daltonik, GmbH, Bremen (DE)" by
-- Bruker Chemical Analysis BV, Middelburg (NL) --

Signed and Sealed this
Eighth Day of October, 2013

Teresa Stanek Rea
*Deputy Director of the United States Patent and Trademark Office*